United States Patent [19]

Whelan

[11] Patent Number: 5,000,735
[45] Date of Patent: Mar. 19, 1991

[54] SINGLE USE SYRINGE

[75] Inventor: James P. Whelan, Olney, Md.

[73] Assignee: The Regents of the Univ. of California, Berkeley, Calif.

[21] Appl. No.: 294,061

[22] Filed: Jan. 5, 1989

[51] Int. Cl.$^5$ ............................................. A61M 5/00
[52] U.S. Cl. ................................... 604/110; 604/236; 604/238
[58] Field of Search ............... 604/110, 228, 187, 218, 604/236, 238, 246, 247

[56] References Cited

U.S. PATENT DOCUMENTS

| | | |
|---|---|---|
| 3,306,291 | 2/1967 | Burke . |
| 3,478,937 | 11/1969 | Solowey . |
| 3,667,657 | 6/1972 | Chiquiar-Airas . |
| 3,890,971 | 6/1975 | Leeson et al. . |
| 3,941,128 | 3/1976 | Baldwin ............................. 604/238 |
| 3,951,146 | 4/1976 | Chiquiar-Arias . |
| 3,998,224 | 12/1976 | Chiquiar-Arias . |
| 4,026,287 | 5/1977 | Haller . |
| 4,233,975 | 11/1980 | Yerman . |
| 4,252,118 | 2/1981 | Richard et al. . |
| 4,266,544 | 5/1981 | Wardlaw . |
| 4,332,323 | 6/1982 | Reenstierna . |
| 4,367,738 | 1/1983 | Legendre et al. . |
| 4,391,272 | 7/1983 | Staempfli . |
| 4,391,273 | 7/1983 | Chiquiar-Arias . |
| 4,479,801 | 10/1984 | Cohen ................................. 604/238 |
| 4,493,703 | 1/1985 | Butterfield . |
| 4,634,428 | 1/1987 | Cuu . |
| 4,650,468 | 3/1987 | Jennings, Jr. . |
| 4,675,005 | 6/1987 | DeLuccia . |
| 4,687,467 | 8/1987 | Cygielski . |
| 4,699,614 | 10/1987 | Glazier . |
| 4,710,170 | 12/1987 | Haber et al. . |
| 4,713,056 | 12/1987 | Butterfield . |
| 4,728,321 | 3/1988 | Chen . |
| 4,731,068 | 3/1988 | Hesse . |
| 4,923,443 | 5/1990 | Greenwood et al. ............... 604/110 |

FOREIGN PATENT DOCUMENTS

| | | |
|---|---|---|
| 1500009 | 11/1967 | France . |
| 2298340 | 8/1976 | France . |
| 1150980 | 5/1969 | United Kingdom . |

Primary Examiner—John D. Yasko
Attorney, Agent, or Firm—Poms, Smith, Lande & Rose

[57] ABSTRACT

A hyperdermic syringe having a plunger which separates from a piston inside a barrel of the syringe after a downward stroke of the plunger preventing reuse of the syringe. The plunger breaks breakaway portions mounted inside the piston when pushed downward to unload the syringe effectively separating the plunger from the piston and destroying the syringe, preventing the piston from being withdrawn for the purpose of reloading the syringe. In another embodiment, a connector is used to releasably engage a plunger to a piston. Downward movement of the plunger causes upward extensions of the connector to move toward each other and lock together. The plunger disengages from the connector and piston after the extension lock together. A modified tip portion of a barrel containing a valve ball and valve flaps may be used to prevent the syringe from being used after a single use discharging medicinal fluid from the syringe. The valve ball blocks flow of medicinal fluid into the syringe after use of the syringe. The modified tip portion may be used alone or in conjunction with the designs which disengage the plunger from the piston after a single use of the syringe.

15 Claims, 5 Drawing Sheets

SINGLE USE SYRINGE

BACKGROUND OF THE INVENTION

The present invention relates generally to hypodermic syringes and, more particularly, to a hypodermic syringe having a plunger which separates from a piston in a barrel of the syringe after a downward stroke of the plunger preventing further use of the syringe.

The increase in infectious diseases such as AIDS, hepatitis, etc., and the use of syringes by drug users have led to increased incidents of blood-borne diseases resulting from the reuse or sharing of syringes. One way of alleviating this problem is by providing syringes that may be used only one time. If a syringe breaks or is self-destroying when used a first or single time, then the syringe becomes useless after a single injection and will have to be discarded preventing reuse of the syringe. It would be desirable for such a single use syringe to be easy to use and relatively inexpensive to manufacture.

In the past, a number of disposable syringes have been proposed. For example, disposable syringes having rods, pins, knives or cutting edges used to puncture or cut the barrels or other parts of the syringes upon first use of the syringes are disclosed in U.S. Pat. Nos. 4,687,467, issued to Cygielski on Aug. 18, 1987; 4,391,273, issued to Chiquiar-Arias on July 5, 1983; 3,998,224, issued to Chiquiar-Arias on Dec. 21, 1976; 3,951,146 issued to Chiquiar-Arias on Apr. 20, 1976; and 3,667,657, issued to Chiquiar-Arias on June 6, 1972; and French Patent No. 2,298,340 to Blanie, dated Aug. 20, 1976. However, these types of syringes may present problems because the syringes will leak if users attempt to reuse the syringes after they are cut or punctured. Also, when a syringe is punctured by pushing a pin or rod through the forward portion of the syringe barrel, it may be possible to avoid damage to the syringe and allow reuse of the syringe by not pushing the syringe plunger all the way to the front of the barrel.

Some syringes may be reused even though they were intended to be used as disposable or non-reusable syringes. For example, U.S. Pat. Nos. 4,675,005, issued to DeLuccia on June 23, 1987, and 4,026,287, issued to Haller on May 31, 1977, disclose syringes having a piston that engages a forward needle-supporting portion of the syringe pulling the portion free of the syringe barrel toward the back of the syringe upon withdrawal of the syringe plunger. Nevertheless, this type of syringe may be reused by simply not pushing the piston all the way to the front of the syringe, thereby avoiding engagement with the forward needle-supporting portion. U.S. Pat. No. 4,650,468, issued to Jennings Jr. on Mar. 17, 1987, describes a syringe having a plunger that may be used to retract a forward needle-supporting portion toward the back of the syringe where it may be locked in place preventing reuse of the syringe by moving the plunger forward for an injection until it engages the needle-supporting portion and then rotating the plunger until the portion separates from the barrel of the syringe, allowing the portion to be pulled to the back of the syringe. This type of syringe may be reused by not rotating the plunger after each injection.

U.S. Pat. No. 3,478,937, issued to Solowey on Nov. 18, 1969, shows a syringe that has a disc attached near the rear of a plunger that is locked to the back of the syringe, making the syringe inoperable, by pushing a piston attached to the front of the plunger toward the front of the syringe. Once again, this type of syringe may be reused by simply not pushing the piston all the way to the front of the syringe preventing the disc from locking to the rear of the syringe. A piston attached to a plunger in U.S. Pat. No. 4,233,975, issued to Yerman on Nov. 18, 1980, is pushed forward until it forces a plugging member to block the needle passageway at the front of the syringe, preventing fluid from exiting the syringe. This syringe may be reused by pushing the piston only part of the way forward so that the passageway is not blocked.

Syringes having a piston that is locked to the front of the syringe barrel when a plunger is pushed forward for an injection are described in U.S. Pat. Nos. 4,713,056, issued to Butterfield on Dec. 15, 1987, and 4,391,272, issued to Staempfli on July 5, 1983. A person may reuse this type of syringe by not pushing the plunger all the way forward, preventing the piston from being locked to the syringe barrel.

Non-reusable syringes prefilled with medicinal fluid to be injected into a patient which have plungers that move in only one direction toward the front of the syringes are disclosed in U.S. Pat. Nos. 4,493,703, issued to Butterfield on Jan. 15, 1985; 4,367,738, issued to Legendre, et al. on Jan. 11, 1983; and 4,252,118, issued to Richard, et al. on Feb. 24, 1981. None of the syringes described in these three patents have a plunger which may be retracted toward the rear of a syringe for the purpose of filling the barrel of the syringe with the medicinal fluid needed for an injection. As a result, all of these syringes must be prefilled with needed medicinal fluid and can only be used to inject one type of prefilled fluid. Unlike the above three syringes, a syringe having a plunger that can be withdrawn for the purpose of filling or loading the syringe can be used to inject any type of medicinal fluid. U.S. Pat. No. 4,252,118, issued to Richard et al. on Feb. 24, 1981, describes a syringe having a plunger which detachably engages a piston. A slight rearward pressure may be applied to the plunger shown in this patent to draw some fluid from a patient in order to perform a "vein test" to make sure that the needle is not improperly placed in the patient, but the plunger cannot be withdrawn for the purpose of filling or loading the syringe with medicinal fluid needed for an injection without disconnecting the plunger from the piston.

A syringe having a connector, attached to a piston, which engages a Z-shaped guide groove in a plunger inside a barrel of the syringe is disclosed in U.S. Pat. No. 4,699,614, issued to Glazier on Oct. 13, 1987. The syringe may be filled with medicinal fluid by withdrawing the plunger toward the back of the syringe. The piston and connector disengage from the Z-shaped guide groove in the plunger following an injection of the fluid from the syringe. However, the syringe is not destroyed after a single use and it may be possible to engage the connector to the Z-shape guide groove in the plunger for another use of the syringe if a user is willing to spend enough time and effort to accomplish this task. A second syringe design is shown in this patent which uses liquid adhesive contained in a cavity of a collar holder attached to a piston to cement together the parts of the syringe preventing reuse thereof after a plunger is withdrawn following an injection. The withdrawn plunger pulls a filament or cord attached to a cap covering the cavity causing the cap to pull free and the adhesive to spill into the barrel of the syringe. Nevertheless, this syringe may be reused by not retracting the plunger all the way back after an injection in order to prevent the cap from pulling free of the cavity.

Different non-reloadable syringe embodiments are described in U.S. Pat. No. 4,731,068, issued to Hesse on Mar. 15, 1988, which allow a plunger to go through one complete cycle of being withdrawn to load the syringe with medicinal fluid and then being pushed forward to inject the fluid. However, the designs of these embodiments are complicated and expensive and do not facilitate simple modifications of existing syringe designs. Another expensive and complicated syringe design is shown in U.S. Pat. No. 3,890,971, issued to Leeson, et al. on June 24, 1975. This syringe uses an ampule prefilled with medicine and is not intended for use with different medicinal fluids.

Syringes that are reusable until the needles or other parts thereof are bent, broken or made inoperative are disclosed in U.S. Pat. Nos. 4,728,321, issued to Chen on Mar. 1, 1988 (needle cemented to cap); 4,710,170, issued to Habner, et al. on Dec. 1, 1987 (needle bent by plunger in barrel of syringe); 4,634,428, issued to Cuu on Jan. 6, 1987 (device in cover used to bend needle); 4,332,323, issued to Reenstierna on June 1, 1982 (projections in sleeve used to bend needle); 4,266,544, issued to Wardlaw on May 12, 1981 (device mounted at front of syringe used to bend needle); and 3,306,291, issued to Burke on Feb. 28, 1967 (lateral movement breaks boss portion of barrel of syringe).

Other syringes are disclosed in British Patent No. 1,150,980 to Husted-Andersen, dated May 7, 1969; and French Patent No. 1,500,009 to Auberlinder, dated Nov. 3, 1967.

Accordingly, there is a need for a single use hypodermic syringe having a plunger, engaged to a piston, which may be withdrawn to load the syringe with medicinal fluid, pushed forward to inject the fluid, and then retracted after the injecting causing the plunger to separate from the piston destroying the syringe and preventing reuse of the syringe. Such a syringe should be inexpensive to fabricate and easy to adapt to existing syringe designs.

SUMMARY OF THE INVENTION

It is an object of the present invention to provide a syringe which may be used only one time to prevent the sharing of the syringe in order to minimize the likelihood of the spreading of different diseases.

It is another object of the invention to provide a syringe that is self-destructing following a single use, which will not leak after destruction.

It is still another object of the invention to provide a syringe that permits an initial loading of the syringe with medicinal fluid and subsequent injection of the fluid, but prevents reloading of the syringe with additional fluid.

It is still another object of the invention to provide a self-destructible syringe that is relatively easy to manufacture, inexpensive and adaptable to conventional syringe designs.

These and other objects and advantages are attained by a hypodermic syringe having a plunger which separates from a piston inside a barrel of the syringe upon a downward stroke of the plunger, preventing reuse of the syringe. The plunger breaks breakaway portions mounted inside the piston when pushed downward for the purpose of unloading the syringe which separates the plunger from the piston and destroys the syringe, preventing the piston from being withdrawn in order to reload the syringe.

In another embodiment, a connector is used to releasably engage a plunger to a piston. Downward movement of the plunger causes upward extensions of the connector to move toward each other and lock together. The plunger disengages from the connector and piston after the extensions lock together, preventing reuse of the syringe.

In yet another embodiment a modified tip portion of a barrel containing a valve ball and valve flaps may be used to prevent the syringe from being reused after a single use. The valve ball is forced past the valve flaps to the bottom of the tip portion when the syringe is unloaded after a first or single use and remains trapped below the valve flaps. Subsequent attempts to reload the syringe will be prevented by the trapped valve ball which blocks flow of medicinal fluid past the valve flaps into the syringe, preventing reuse of the syringe. The modified tip portion may be used alone or in conjunction with the designs which disengage the plunger from the piston after a single use of the syringe.

The various features of the present invention will be best understood together with further objects and advantages by reference to the following description of the preferred embodiments taken in conjunction with the accompanying drawings.

DESCRIPTION OF THE PREFERRED EMBODIMENTS

Figure 1:
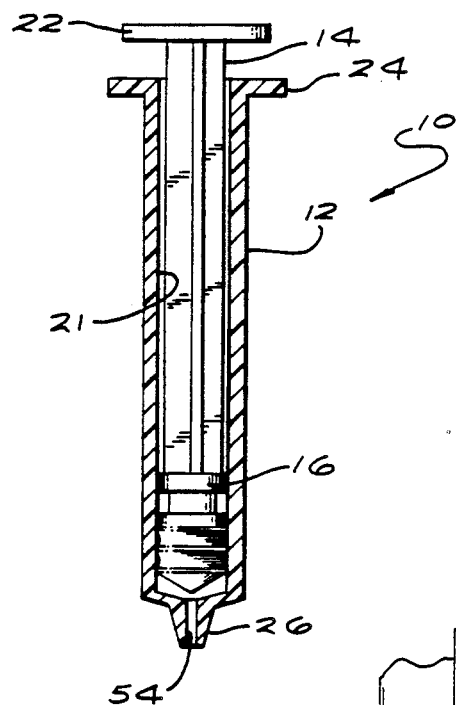
FIG. 1 is a partial cross-sectional elevational view of a single use syringe illustrating the principles of the present invention.

The following specification taken in conjunction with the drawings sets forth the preferred embodiments of the present invention in such a manner that any person skilled in the art can use the invention. The embodiments of the invention disclosed herein are the best modes contemplated by the inventor for carrying out his invention in a commercial environment although it should be understood that various modifications can be accomplished within the parameters of the present invention.

FIGS. 1 through 8 show a preferred embodiment of the single use hypodermic syringe 10 of the present invention. They syringe 10 has a hollow cylindrically-shaped barrel 12. A plunger 14 is inside the interior of the barrel 12. A plunger seat 16 is attached to the forward end of the plunger 14 and a plunger extension 18 is attached to the seat 16 and extends downward or forward therefrom. A piston 20 is releasably engaged to extension 18 as explained in the following discussion. The piston 20 is preferably made out of rubber and slidably engages the interior walls 21 of the barrel 12 so that a seal is provided between the piston 20 and the interior walls 21. A thumb rest 22 is attached to the top or back end of the plunger 14 and finger grips 24 are attached to the top end of the barrel 12. Thumb rest 22 and finger grips 24 allow a user to selectively push down on the rest 22 causing the piston 20 and plunger 14 to move forward, or to grasp the rest 22 and pull or withdraw the piston 20 and plunger 14 toward the back of the syringe 10. The barrel 12 has a tip portion 26 at the forward end thereof.

Figure 2:
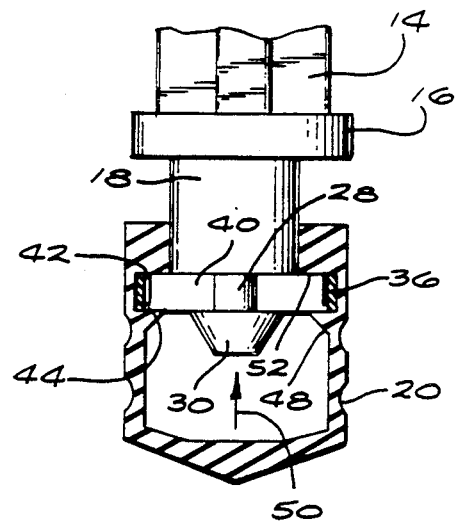
FIG. 2 is an enlarged partial cross-sectional view of a piston and the forward end of a plunger of the syringe of FIG. 1 showing how the plunger is engaged to the piston by a tab support ring.
Figure 3:
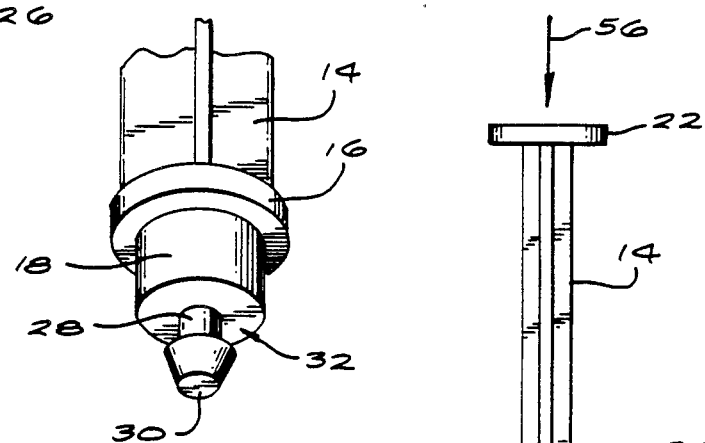
FIG. 3 is an enlarged perspective view of the forward end of the plunger.
Figure 4:
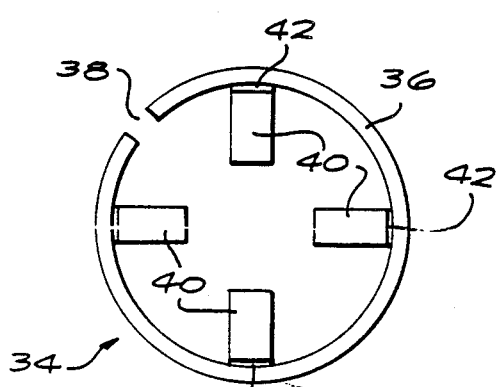
FIG. 4 is a top plan view of the tab support ring.

Referring now to FIGS. 2 through 4, the plunger extension 18 has a connection 28 attached to it connecting a plunger tip 30 to the extension 18 so that an annular groove 32 is formed between the extension 18 and the tip 30. A tab support ring 34 shown in FIG. 4 has an annular ring portion 36 with an opening 38 therein which allows the ring 34 to be compressed or expanded so that it may be installed or mounted in groove 32 and inside the piston 20 as explained below. Attached to the inside diameter of the ring portion 36 are breakaway portions or tabs 40 which extend radically inward from portion 36. Each tab 40 has a vertical slot 42 thereon passing through the top surface thereof vertically downward as shown in FIG. 2 so that the tabs 40 are separated from the ring portion 36 except where connecting portions 44 attach the tabs 40 to the ring portion 36. The tab support ring 34 is mounted in annular groove 32 between the plunger extension 18 and tip 30 and inside the hollow piston 20 as shown in FIG. 2 so that the ring 34 fits into an annular groove 46 inside the piston 20 (see FIG. 7).

When the plunger 14 is pulled or withdrawn upward as indicated by arrow 50 in FIG. 2, the plunger tip 30 pushes upward on the tabs 40 causing the top surfaces of tabs 40 to contact upper surface 52 of annular groove 46 while the bottom surfaces of the tabs 40 are supported by annular ledge 48 inside the piston 20. As a result, piston 20 moves upward with the plunger 14. As the piston 20 is withdrawn or moves upward, medicinal fluid may be drawn inside barrel 12 of the syringe 10 through aperture 54 in tip portion 26, or the syringe 10 may be loaded with medicinal fluid later to be injected into a patient. The plunger 14 is shown withdrawn toward the back of the syringe 10 in FIG. 5 after the syringe 10 has been loaded.

Figure 5:
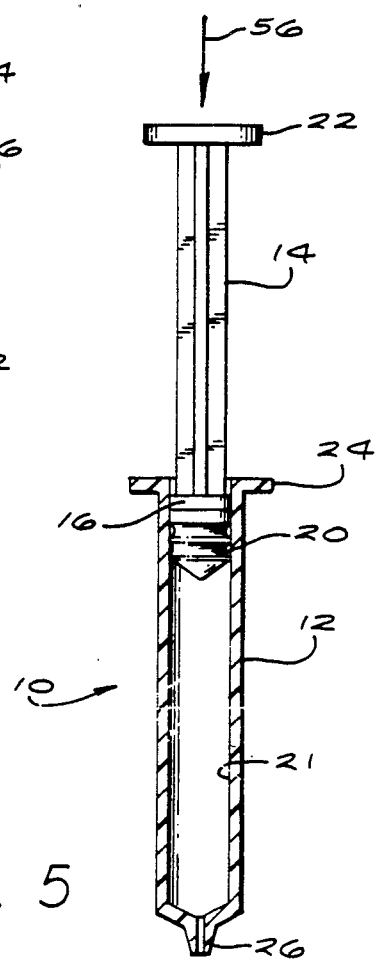
FIG. 5 is a view taken similar to FIG. 1 showing the plunger and piston being pushed downward at the start of an injection after loading the syringe.
Figure 6:
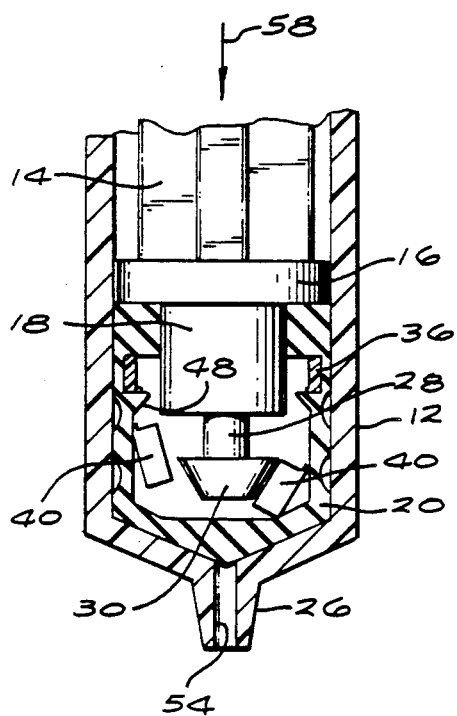
FIG. 6 is a view taken similar to FIG. 2 showing how the forward end of the plunger shears off tabs connected to the tab support ring when the plunger and piston are pushed toward the front of the syringe for an injection.

After the syringe 10 is loaded, a user may press downward on the thumb rest 22 causing the plunger 14 to move downward or forward as indicated by arrows 56 and 58 shown in FIGS. 5 and 6 for the purpose of unloading the medicinal fluid in the barrel or giving an injection to a patient by forcing the fluid out of the barrel through aperture 54 in tip portion 26. However, as the plunger 14 moves downward, plunger extension 18 also moves downward and causes the breakaway tabs 40 to tear away from the ring portion 36 as connecting portions 44 are broken because ledge 48 does not provide sufficient support for the tabs 40 and slots 42 facilitate separation of the tabs 40 from ring portion 36. After the tabs 40 break away, the plunger seat 16 contacts and pushes against the top of piston 20 as shown in FIG. 6 so that the plunger 14 continues to force the piston 20 downward until it reaches the bottom or forward end of the barrel 12 and the medicinal fluid is unloaded through aperture 54.

Figure 7:
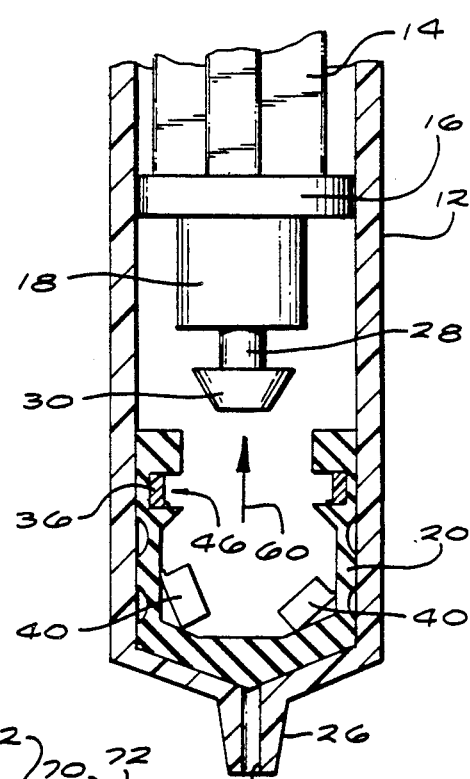
FIG. 7 is a view taken similar to FIG. 2 showing how the forward end the plunger disengages from the piston when withdrawn toward the back of the syringe after an injection.
Figure 8:
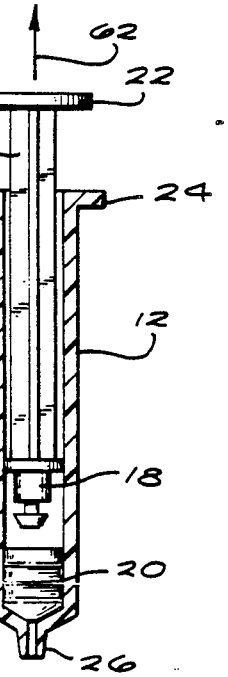
FIG. 8 is a view taken similar to FIG. 1 showing the plunger disengaged from the piston after the syringe is unloaded and the plunger is withdrawn toward the back of the syringe.

FIGS. 7 and 8 show how the forward end of the plunger 14 disengages from the piston 20 after the syringe 10 has been unloaded by pushing the piston to the bottom of the barrel 12 and the plunger 14 is withdrawn toward the back of the syringe 10 as indicated by arrows 60 and 62, leaving the piston 20 at the front of the syringe 10. As a result, the syringe 10 is destroyed after the medicinal fluid has been discharged out of the syringe 10 through aperture 54 because the piston 20 will remain at the front of the syringe 10 or bottom of the barrel 12 and cannot be withdrawn for the purpose of reloading the syringe with medicinal fluid. Therefore, syringe 10 cannot be reused after a single use, or after medicinal fluid has been drawn into the syringe 10 and subsequently discharged from the syringe 10 for an injection as described above.

Figure 9:
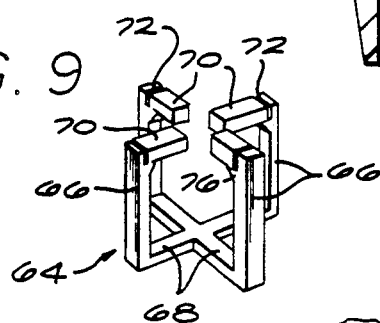
FIG. 9 is a perspective view of another embodiment of a tab support.
Figure 10:
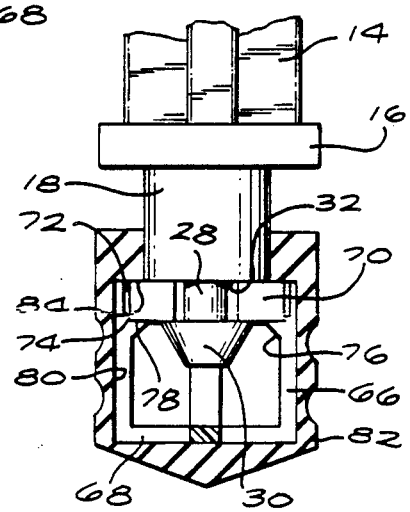
FIG. 10 is an enlarged partial cross-sectional view of a piston and the forward end of a plunger of the syringe of FIG. 1 showing how the plunger is engaged to another embodiment of a piston by the tab support of FIG. 9.

Another embodiment of a tab support 64 is shown in FIGS. 9 and 10. Ring 64 has vertical tab supports 66, preferably formed integrally with and supported by horizontal tab supports 68. Breakaway portions, or tabs 70 are attached to the tops of supports 66 and have vertical slots 72 passing vertically downward as shown in FIGS. 9 and 10 so that the tabs 70 are separated from supports 66 except where connecting portions 74 attach the tabs 70 to the supports 66. Each tab 70 has a ledge 76 which is separated from the tab 70 by horizontal slot 78. The tab support 64 fits inside internal bore 80 in another embodiment of a piston 82 and tabs 70 engage annular groove 32 at the forward end of the plunger 14 as shown in FIG. 10.

When the plunger 14 is withdrawn for the purpose of loading the syringe 10, plunger tip 30 pushes upward on tabs 70 causing the top surfaces of the tabs 70 to push against internal surface 84 of the piston 82 while the bottom surfaces of the tabs 70 are supported by ledges 76. However, when the plunger is pushed downward or toward the front of the syringe 10 for the purpose of unloading the syringe 10, plunger extension 18 causes the tabs 70 to tear away from the vertical tab supports 66 as connecting portions 74 are broken because ledges 76 do not provide adequate support for the tabs 70 and slots 72 facilitate separation of the tabs 70 from supports 66. After the tabs 70 have broken away, plunger seat 16 contacts the top of piston 82 forcing the piston 82 to move to the front of the syringe 10 unloading medicinal fluid from the syringe 10. As such, the plunger 14 disengages from piston 82 due to tabs 70 breaking free of supports 66 after the syringe 10 has been unloaded by pushing the plunger 14 and piston 82 to the bottom of the syringe barrel 12, preventing reuse of the syringe 10 because the syringe 10 cannot be reloaded.

Figure 11:
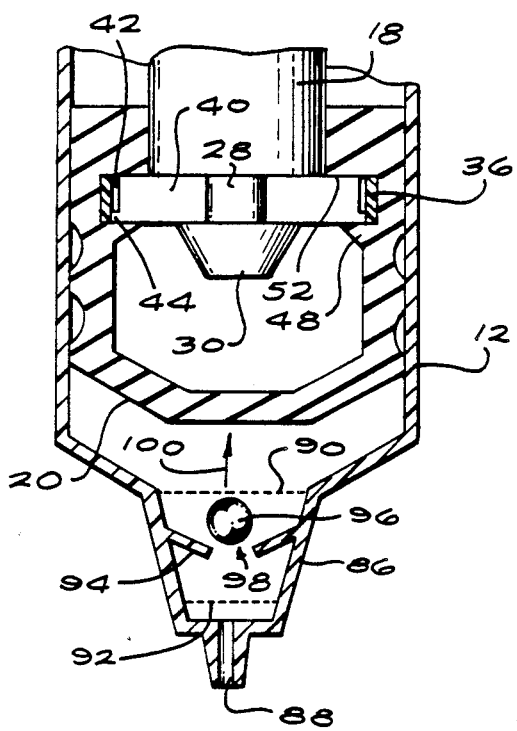
FIG. 11 is a partial cross-sectional view of the piston taken similar to FIG. 2 and of a modified tip portion at the forward end of a barrel of the syringe of FIG. 1 showing a valve ball trapped between upper and lower meshes in the tip portion and above valve flaps when the plunger is being withdrawn toward the back of the syringe.
Figure 12:
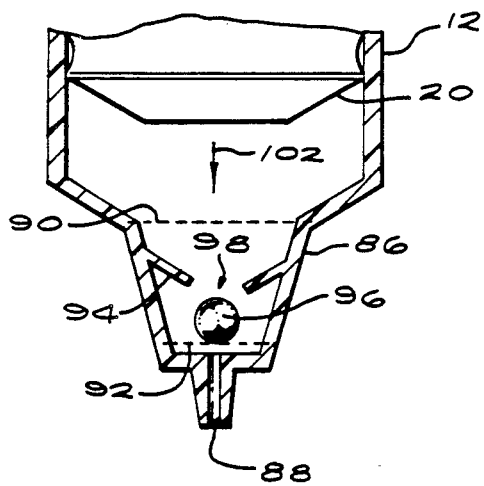
FIG. 12 is a view taken similar to FIG. 11 showing how the valve ball passes the valve flaps which are bent downward when the plunger is pushed forward for an injection.
Figure 13:
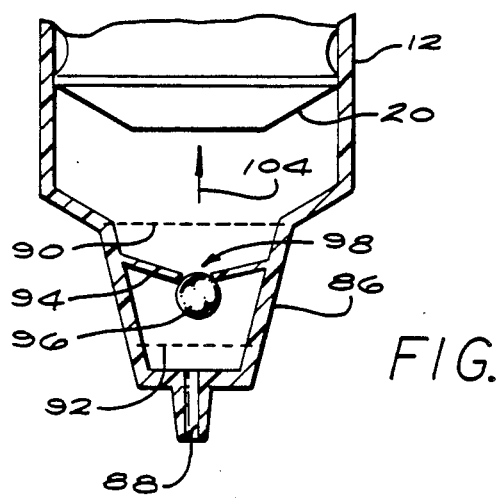
FIG. 13 is a view taken similar to FIG. 11 showing how the valve ball is unable to move upward past the valve flaps which are no longer bent downward when the plunger is withdrawn after an injection.

FIGS. 11 through 13 show another embodiment of the syringe 10 of the present invention having a hollow modified tip portion 86 with an aperture 88 at the end thereof for discharging medicinal fluid from the syringe 10. The modified tip portion 86 may be used alone or in conjunction with any of the disengagable plunger designs of FIGS. 1 through 10, previously discussed, or FIGS. 14 through 24, discussed below, but by way of example only and not limitation, the design of FIG. 2 is shown inside barrel 12 in FIG. 11 for purposes of illustrating how the modified tip coacts with the disengagable plunger design. Mounted inside portion 86 are upper and lower meshes 90 and 92, respectively, which allow medicinal fluid needed for an injection to pass therethrough. The meshes 90 and 92 may be made out of any previous or porous material, or may be fabricated from a screen, interlocking strands, woven material, or the like. Preferably, meshes 90 and 92 are made out of plastic material. Valve flaps 94 are attached to the inside walls of tip portion 86. Before the first use of the syringe 10, a valve element or ball 96 is initially located inside the tip portion 86 between the valve flaps 94 and the upper mesh 90 as shown in FIG. 11. Any size or shape valve element or ball 96 may be used that will block fluid flow through the tip portion 86 as explained below. The valve flaps 94 are sized and made out of a material such as plastic, or the like, which provides flexibility and resiliency allowing the flaps 94 to bend upward and downward in reaction to changes in fluid flow and pressure inside tip portion 86 resulting from upward and downward movement of the piston 20.

A syringe 10 with the tip portion 86 shown on FIGS. 10 through 13 is provided to a user before the first use thereof with the valve ball 96 located above the valve flaps 94. When the valve ball 96 is located in its position, aperture 98 formed by flags 94 is not large enough to allow the ball 96 to pass through it. In addition, when the piston 20 is withdrawn as indicated by arrow 100 in FIG. 11 to load the syringe 10 with medicinal fluid, the valve ball 96 is drawn upward by resulting fluid flow and pressure, but is prevented by upper mesh 90 from moving upward into the barrel 12. Therefore, the syringe 10 may be loaded with medicinal fluid by withdrawing the piston 20 or plunger 14 which allows the fluid to pass through aperture 88 into hollow tip portion 86, past lower mesh 92, through aperture 98 formed by valve flaps 94, and past upper mesh 90 into the barrel 12 of the syringe 10.

FIG. 12 shows how the aperture 98 opens when the piston 20 is pushed forward as indicated by arrow 102 in order to give an injection to a patient. As the medicinal fluid is forced out of the syringe 10 through aperture 88 by pushing the plunger 14 and piston 20 to the front of the syringe 10, fluid flow and pressure acting on the valve ball 96 cause the valve flaps 94 to bend downward enlarging aperture 98 to allow valve ball 96 to pass through the enlarged aperture 98 toward the bottom of tip portion 86 where further downward movement is restricted by lower mesh 92 as shown. Note that the lower mesh 92 prevents the valve ball 96 from blocking aperture 88 during unloading of the syringe 10. After fluid has been discharged from the syringe 10, valve flaps 94 return to their original unflexed position returning aperture 98 to its original size, but the valve ball 96 remains trapped between the flaps 94 and lower mesh 92 and is unable to move past flaps 94 or pass through aperture 98 which has returned to its smaller original size. As a result, any attempt to withdraw the plunger 14 and piston 20 for the propose of reloading the syringe 10 as indicated by arrow 104 in FIG. 13 will cause the valve flaps 94 to bend upward decreasing the size of aperture 98 and the valve ball 96 to block aperture 98 as shown preventing medicinal fluid from passing through aperture 98 into barrel 12 of the syringe 10. Therefore, the syringe 10 cannot be reused after a first use has discharged fluid from the syringe 10 because valve ball 96 will block medicinal fluid flow through aperture 98.

Valve ball 96 is preferably made out of plastic, but any suitable material may be used. Also, any shape element or ball 96 may be used that will effectively block fluid flow through aperture 98. It is important to note that the modified tip portion 86 with valve ball 96, valve flaps 94 and meshes 90 and 92 may be used alone or in conjunction with the disengagable plunger designs of FIGS. 1 through 10, previously discussed, or the disengagable plunger designs of FIGS. 14 through 24 discussed below. As such, the modified tip portion 86 functions like a valve means for a regulating fluid flow through aperture 88 and may be used as a backup to the other disengagable plunger designs of the present invention to better ensure that the syringe 10 may be used only one time. Thus, when the modified tip portion 86 is used in combination with one of the disengagable plunger designs, efforts to reuse the syringe 10 after a single use by somehow jamming or otherwise re-engaging the plunger 14 to the piston 20 would be defeated by tip portion 86 which coacts with the other designs to prevent reuse of the syringe 10.

Figure 14:
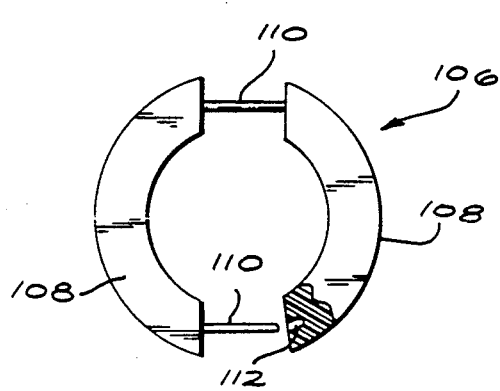
FIG. 14 is a top plan view of another embodiment of a support ring with breakaway connectors.
Figure 15:
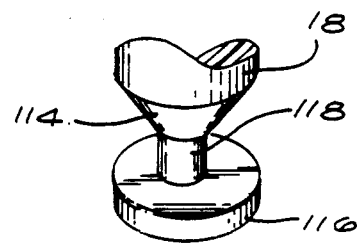
FIG. 15 is a perspective view of another embodiment of a plunger with a frustro-conically-shaped portion at the forward end thereof.

FIG. 14 shows another embodiment of a support ring 106 that may be used with the present invention of syringe 10. The ring 106 has two ring halves 108 held together by breakaway portions or connectors 110 which are elongated members. Preferably, an end of one of the connectors 110 engages socket 112 in an end of one of the halves 108 to complete the connection of the two halves 108 to each other. The end of connector 110 may be press fit, cemented, or otherwise placed into socket 12. As a result, the support ring 106 may be easily installed around the modified design of the forward end of the plunger 14 shown in FIGS. 15 and 16. The forward end of the plunger 14 has a frustro-conically-shaped portion 114 extending downward from the plunger extension 18 and a bottom portion 116 attached to portion 114 by connector 118. The support ring 106 and forward end of plunger 14 are installed inside another embodiment of a piston 120 with the ring 106 engaging annular groove 122 (see FIG. 16) inside the piston 120 and the forward end of the plunger 14 fitting into internal bore 124 of the piston 120. As such, the support ring 106 removably engages the plunger 14 to the piston 120.

Figure 16:
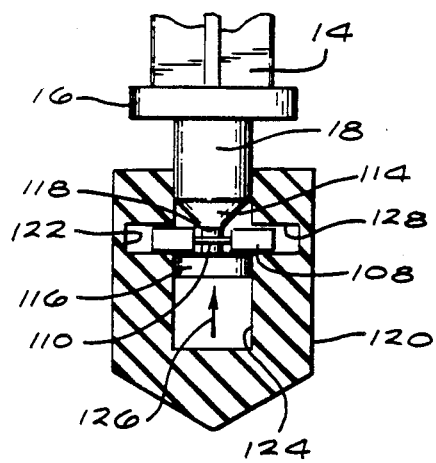
FIG. 16 is an enlarged partial cross-sectional view of another embodiment of a piston, the support ring of FIG. 14 and the plunger of FIG. 15 used for the syringe of FIG. 1 showing how the plunger is connected to the piston by the support ring.
Figure 17:
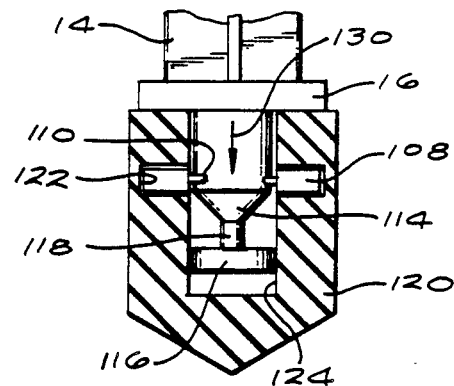
FIG. 17 is a view taken similar to FIG. 16 showing how the plunger separates two halves of the support ring causing the connectors to break when the plunger is pushed forward for an injection.

When the plunger 14 is withdrawn, as indicated by arrow 126 in FIG. 16, bottom portion 116 pushes upward on the support ring 106 and the top surfaces of halves 108 press against internal surfaces 128 of groove 122 so that the plunger 14 and piston 120 move toward the back of the syringe 10 allowing it to be filled with medicinal fluid. However, downward movement of the plunger 14 for the purpose of discharging the medicinal fluid from the plunger 14 as indicated by arrow 120 in FIG. 17 disengages the plunger 14 from the piston 120. When the plunger is pushed downward frustro-conically-shaped portion 114 comes into contact with the two halves 108 of the support ring 106 causing the halves 108 to separate and the connectors 110 to break which forces the connectors 110 radially into annual groove 122 as shown in FIG. 17. The forward end of the plunger 14 continues to move downward until seat 16 contacts the top of piston 120 causing the plunger 14 to push the piston 120 to the bottom of the barrel 12 of the syringe 10 thereby unloading the syringe 10.

Figure 18:
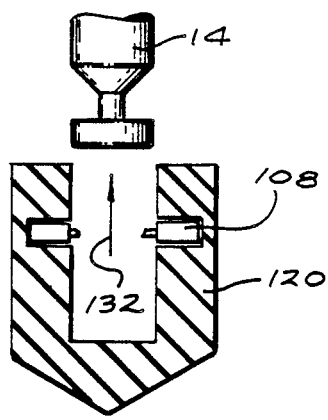
FIG. 18 is a view taken similar to FIG. 16 showing how the plunger disengages from the piston when withdrawn after an injection.

After the plunger 14 and piston 120 have been pushed forward to unload the syringe 10 causing the connectors 110 to break away and the halves 108 of the supporting ring 106 to separate, withdrawal of the plunger 14 toward the back of the syringe 10 as indicated by arrow 132 in FIG. 18 results in the plunger 14 disengaging from the piston 120 as shown. As such, the syringe 10 cannot be reused because the piston 120 is unable to be withdrawn for the purpose of reloading the syringe.

Therefore, the syringe 10 is self-destructible after a single use.

Figure 19:
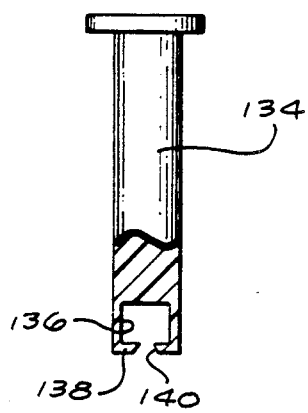
FIG. 19 is a partial cross-sectional elevational view of another embodiment of a plunger having a flange at the forward end thereof.
Figure 20:
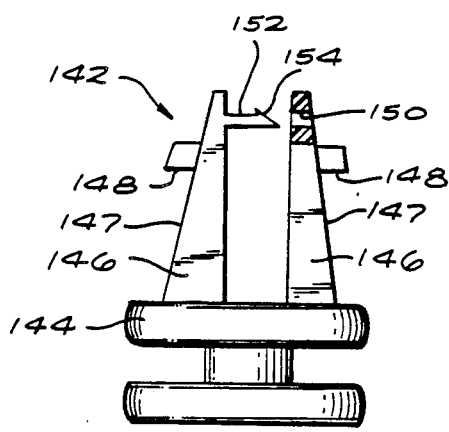
FIG. 20 is an elevational view of a connector used with the plunger
Figure 21:
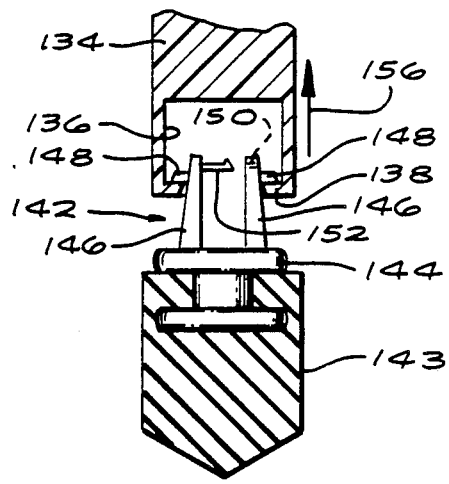
FIG. 21 is a partial cross-sectional view showing how the connector is used to couple the plunger to another embodiment of a piston, all of which are used for the syringe of FIG. 1.

Another embodiment of a plunger 134 used with the syringe 10 is shown in FIG. 19. The plunger 134 has a cylindrical bore 136 at the forward end thereof with a flangee 138 at the open end of the bore 136. The flangee 138 has an inclined surface 140 at the inner circumference thereof. FIG. 20 shows a connector 142 used to removably engage the plunger 134 to another embodiment of a piston 143 as shown in FIG. 21. Note that the plunger 134, connector 142 and piston 143 fit inside the barrel 12 of the syringe 10. The connector 142 has a bottom portion 144 which is attached to the piston 143. Two upward extensions 146 are attached to the top of bottom portion 144. Each of the extensions 146 has a tab 148 attached to it. Both extensions 146 have slanted surfaces 147. One of the extensions 146 has an aperture 150 near the top of it while the other extension 146 has a locking member 152 attached to it capable of engaging aperture 150 so that the top ends of the extensions 146 are held together. Locking member 152 preferably has an engaging portion 154 that prevents member 152 from disengaging from aperture 150 after engagement has occurred.

Figure 22:
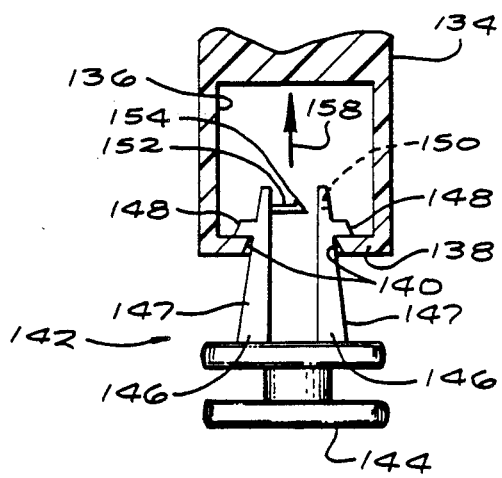
FIG. 22 is an enlarged partial cross-sectional view with the piston omitted showing how the flange of the plunger engages tab extensions of the connector.
Figure 23:
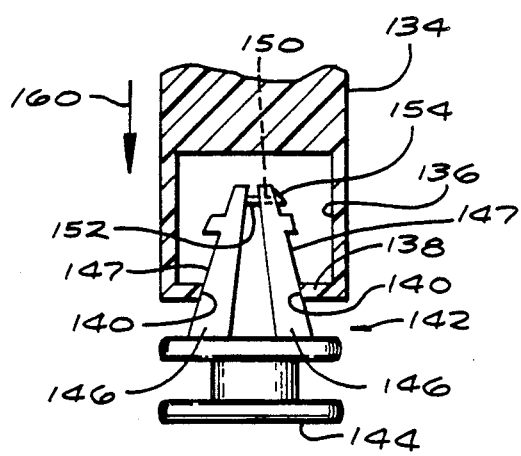
FIG. 23 is a view taken similar to FIG. 22 showing how the flange of the plunger slides down slanted surfaces of two upward extensions of the connector when the plunger is pushed forward for an injection causing the extensions to move toward each other and a locking member near the top of one of the extensions to engage an aperture near the top of the other extension.

As illustrated in FIGS. 21 and 22, flangee 138 of the plunger 134 engages tabs 148 of extensions 146 so that the plunger 134 may be withdrawn with the piston 143 as indicated by arrows 156 and 158 for the purpose of loading the syringe 10. After the syringe 10 has been loaded with medicinal fluid, the plunger 134 is pushed downward as indicated by arrow 160 in FIG. 23 for the purpose of pushing the piston 143 to the front of the syringe 10 in order to unload the syringe 10. Downward movement of the plunger 134 causes inclined surface 140 of flangee 138 to slide down slanted surfaces 147 of the two upward extensions 146 and the extensions 146 to move toward each other until locking member 152 engages aperture 150 so that the upper portions of the extensions 146 are held together with engaging portion 154 preventing member 152 from disengaging from aperture 150. Note that flangee 138 will continue to slide down slanted surfaces 147 until the plunger 138 contacts the top of bottom portion 144 thereby causing the connector 142 and piston 143 to be pushed to the front of the syringe 10 in order to discharge medicinal fluid from the syringe 10.

Figure 24:
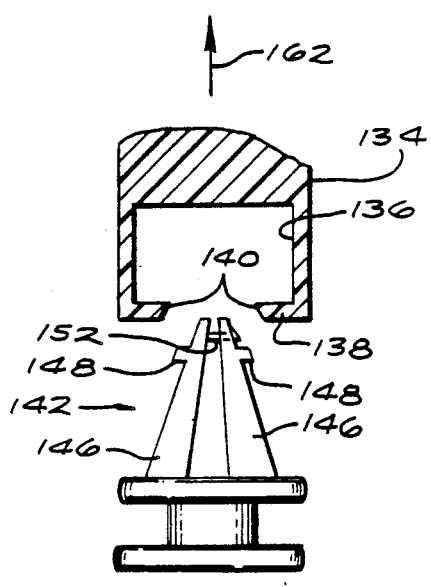
FIG. 24 is a view taken similar to FIG. 22 showing how the plunger disengages from the connector when the plunger is withdrawn after an injection.

After the syringe 10 has been unloaded and the piston has been pushed to the front of the syringe 10, the plunger 134 may be withdrawn as illustrated by arrow 162 in FIG. 24 toward the back of the syringe 10 causing the front end of the plunger 134 to disengage from the connector 142 as flange 138 comes free or clear of tabs 148 due to the upper portions of extensions 146 being held together by locking member 152. As a result, the piston 143 and connector 142 are left at the bottom of barrel 12 of the syringe 10 after the plunger 134 is withdrawn. Since the locking members 152 keep the top ends of extensions 146 together, flanges 138 cannot engage tabs 148 and the plunger can no longer be engaged to the connector 142 or piston 143, preventing reuse of the syringe. As such, the plunger 134 disengages from the piston 143 so that the syringe 10 cannot be reused after the first use of the syringe 10.

The plunger-support ring designs of the present invention shown in FIGS. 1 through 10 and 14 through 18 are relatively inexpensive to fabricate and may be installed in modified pistons which fit into or are adaptable to conventional barrels used for syringes. Moreover, the barrels of the syringes used with these designs do not have to be punctured or cut in order to destroy the syringe of the present invention thereby minimizing the chance that the syringe will leak if a user tries to reuse the syringe after it has been destroyed. The plunger-connector design shown in FIGS. 19 through 24 may also be used with a modified piston design and adapted for use with conventional barrels. This design also minimizes the changes that the syringe will leak if a user tries to reuse the syringe. The barrels of conventional syringes may be modified to incorporate the tip portion design with valve ball and flaps shown in FIGS. 11 through 13. However, conventional plungers and pistons may be used with such a modified barrels.

The above description discloses the preferred embodiments of the present invention. However, persons of ordinary skill in the art are capable of numerous modifications once taught these principles such as, by way of example and not limitation, any type of tab support ring may be used that has portions which are capable of being sheared off by downward movement of the plunger inside the piston, thereby disengaging the plunger from the piston. Further, other types of valves that are capable of allowing only one-way flow in the tip portion of the barrel may be used instead of the valve flags 94 and valve ball 96 disclosed herein. Also, other types of connectors may be used in place of connector 142 described herein that may be squeezed together by downward movement of the plunger and locked in such a condition. Accordingly, it will be understood by those skilled in the art that changes in form and details may be made to the above-described embodiments without departing from the spirit and scope of the invention.

I claim:

1. A single use hypodermic syringe comprising:
   a hollow barrel having interior walls;
   a hollow piston slidably engaging said interior walls of said barrel in order to provide a seal between said piston and said walls;
   a plunger fitting inside said barrel having a forward end releasably engaged to said piston; and
   support means mounted inside said piston for releasably engaging said plunger to said piston so that said plunger is capable of being initially withdrawn in order to fill said barrel with medicinal fluid and capable of being subsequently pushed forward in order to discharge said medicinal fluid from said barrel, said plunger disengaging from said piston upon subsequent withdrawal of said plunger, said support means including breakaway portions capable of being broken by forward movement of said plunger in order to disengage said plunger from said piston, said barrel having valve means at the forward end thereof for regulating flow of said medicinal fluid in and out of said barrel and for preventing flow of said medicinal fluid into said barrel after an initial use of said syringe.

2. The single use hypodermic syringe of claim 1 wherein said valve means comprises a hollow tip portion having an aperture therein attached to said forward end of said barrel, upper and lower meshes mounted inside said tip portion, valve flaps mounted inside said tip portion between said meshes and a valve element located inside said tip portion between said meshes.

3. The single use hypodermic syringe of claim 1 wherein said support means comprises an annular ring portion having said breakaway portions extending radically inward from said ring portion.

4. The single use hypodermic syringe of claim 3 wherein said breakaway portions are tabs, said tabs and said ring portion fitting into an annular groove in said piston, said piston having an annular ledge supporting bottom surfaces of said tabs, said tabs having slots therein and engaging an annular groove in said forward end of said plunger, said ring portion having an opening therein.

5. The single use hypodermic syringe of claim 4 wherein said barrel has a hollow tip portion with an aperture therein at the forward end thereof, upper and lower meshes mounted inside said tip portion, valve flaps mounted inside said tip portion between said meshes and a valve element located inside said tip portion between said meshes.

6. A single use hypodermic syringe comprising:
   a hollow barrel having interior walls;
   a hollow piston slidably engaging said interior walls of said barrel in order to provide a seal between said piston and said walls;
   a plunger fitting inside said barrel having a forward end releasably engaged to said piston; and
   support means mounted inside said piston for releasably engaging said plunger to said piston so that said plunger is capable of being initially withdrawn in order to fill said barrel with medicinal fluid and capable of being subsequently pushed forward in order to discharge said medicinal fluid from said barrel, said plunger disengaging from said piston upon subsequent withdrawal of said plunger, said support means including breakaway portions capable of being broken by forward movement of said plunger in order to disengage said plunger from said piston, said support means comprising vertical tab supports with said breakaway portions attached thereto supported by horizontal tab supports.

7. The single use hypodermic syringe of claim 6 wherein said breakaway portions are tabs, said vertical and horizontal tab supports fitting in an internal bore of said piston, said tabs having slots therein and engaging an annular groove in said forward end of said plunger.

8. The single use hypodermic syringe of claim 7 wherein said barrel has a hollow tip portion with an aperture therein at the forward end thereof, upper and lower meshes mounted inside said tip portion, valve flaps mounted inside said tip portion between said meshes and a valve element located inside said tip portion between said meshes.

9. A single use hypodermic syringe comprising:
   a hollow barrel having interior walls;
   a hollow piston slidably engaging said interior walls of said barrel in order to provide a seal between said piston and said walls;
   a plunger fitting inside said barrel having a forward end releasably engaged to said piston; and
   support means mounted inside said piston for releasably engaging said plunger to said piston so that said plunger is capable of being initially withdrawn in order to fill said barrel with medicinal fluid and capable of being subsequently pushed forward in order to discharge said medicinal fluid from said barrel, said plunger disengaging from said piston upon subsequent withdrawal of said plunger, said support means including breakaway portions capable of being broken by forward movement of said plunger in order to disengage said plunger from said piston, said support means comprising two ring halves held together by said breakaway portions.

10. The single use hypodermic syringe of claim 9 wherein said breakaway portions are elongated connecting members, said forward end of said plunger having a frustro-conically-shaped portion capable of engaging said ring halves in order to separate said halves causing said connecting members to break so that said plunger will disengage from said piston.

11. The single use hypodermic syringe of claim 10 wherein one of said elongated connecting members has an end thereof that engages a socket in one of said ring halves.

12. The single use hypodermic syringe of claim 11 wherein said barrel has a hollow tip portion with an aperture therein at the forward end thereof, upper and lower meshes mounted inside said tip portion, valve flaps mounted inside said tip portion between said meshes and a valve element located inside said tip portion between said meshes.

13. A single use hypodermic syringe comprising:
a hollow barrel having interior walls and a hollow tip portion with an aperture therein at a forward end of said barrel;
a hollow piston slidably engaging said interior walls of said barrel in order to provide a seal between said piston and said walls;
a plunger fitting inside said barrel having a forward end engaged to said piston; and
valve means inside said tip portion for regulating flow of medicinal fluid in and out of said aperture in said tip portion and for preventing flow of said medicinal fluid into said aperture after an initial use of said syringe, said valve means adapted to respond solely due to changes in fluid pressure in order to prevent said flow of said medicinal fluid into said aperture after said initial use, said valve means including a valve element and valve flaps, said valve element and valve flaps being adapted so that said flow of said medicinal fluid into said aperture is prevented after said initial use of said syringe.

14. A single use hypodermic syringe comprising:
a hollow barrel having interior walls and a hollow tip portion with an aperture therein at the forward end of said barrel;
a hollow piston slidably engaging said interior walls of said barrel in order to provide a seal between said piston and said walls;
a plunger fitting inside said barrel having a forward end engaged to said piston; and
valve means inside said tip portion for regulating flow of medicinal fluid in an dout of said aperture in said tip portion and for preventing flow of said medicinal fluid into said aperture after an initial use of said syringe, said valve means comprising upper and lower meshes mounted inside said tip portion, valve flaps mounted inside said tip portion between said meshes and a valve element located inside said tip portion between said meshes.

15. The single use hypodermic syringe of claim 14 wherein said valve element is capable of passing downward through an aperture formed by said valve flaps as said flaps bend downward from an original position when said plunger and said piston are pushed downward to discharge said medicinal fluid out of said tip portion through said aperture in said tip portion, said valve element prevented from passing upward from below said valve flaps through said aperture formed by said flaps after said flaps return upward to said original position when said plunger and said piston are withdrawn upward so that said valve element blocks flow of said medicinal fluid through said aperture formed by said flaps.

* * * * *